(12) United States Patent
Condie et al.

(10) Patent No.: US 7,123,965 B2
(45) Date of Patent: Oct. 17, 2006

(54) METHOD AND APPARATUS FOR INJECTION OF EXTERNAL DATA WITHIN AN IMPLANTABLE MEDICAL DEVICE

(75) Inventors: Catherine R. Condie, Shoreview, MN (US); Gerald A. Portzline, Fridley, MN (US); Yong Kyun Cho, Maple Grove, MN (US); John S. Brandstetter, Coon Rapids, MN (US); Luc R. Mongeon, Minneapolis, MN (US); Lucy M. Nichols, Maple Grove, MN (US); Steve R Hornberger, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 505 days.

(21) Appl. No.: 10/137,171

(22) Filed: Apr. 30, 2002

(65) Prior Publication Data

US 2003/0204147 A1    Oct. 30, 2003

(51) Int. Cl.
*A61N 1/365* (2006.01)
(52) U.S. Cl. .................. 607/30; 607/18; 600/510
(58) Field of Classification Search ........... 607/17–19, 607/30, 32; 600/510
See application file for complete search history.

(56) References Cited

U.S. PATENT DOCUMENTS

| | | | |
|---|---|---|---|
| 4,375,674 A * | 3/1983 | Thornton | 702/41 |
| 4,873,980 A * | 10/1989 | Schaldach | 607/27 |
| 5,562,711 A | 10/1996 | Yerich et al. | |
| 5,749,907 A | 5/1998 | Mann | |
| 5,904,708 A * | 5/1999 | Goedeke | 607/18 |
| 6,022,322 A | 2/2000 | Prutchi | |
| 6,622,043 B1 | 9/2003 | Kraus et al. | 607/27 |
| 2003/0181290 A1* | 9/2003 | Black | 482/8 |

FOREIGN PATENT DOCUMENTS

WO     WO 01/23040 A1    4/2001

* cited by examiner

*Primary Examiner*—George R. Evanisko
(74) *Attorney, Agent, or Firm*—Michael C. Soldner; Girma Wolde-Michael

(57) ABSTRACT

A method and an apparatus for performing implementing external data into an implantable medical device. A first stress test is performed using an external sensor. External data resulting from the initial stress test is acquired. An external data injection process is performed. The external data injection process includes providing the external data to the implantable medical device. A second stress test is performed, the second stress test being substantially similar to the first stress test. Internal data resulting from the second stress test is acquired. Internal data resulting from the second stress test along with the external data resulting from the first stress test, are processed.

10 Claims, 9 Drawing Sheets

METHOD AND APPARATUS FOR INJECTION OF EXTERNAL DATA WITHIN AN IMPLANTABLE MEDICAL DEVICE

BACKGROUND OF THE INVENTION

The present invention relates generally to control of implantable medical devices, and, more particularly, the present invention relates to a method and apparatus for implementing external data within an implantable medical device.

DESCRIPTION OF THE RELATED ART

The technology explosion in the implantable medical device industry has resulted in many new and innovative devices and methods for analyzing and improving the health of a patient. The class of implantable medical devices now includes pacemakers, implantable cardioverters, defibrillators, neural stimulators, and drug administering devices, among others. Today's state-of-the-art implantable medical devices are vastly more sophisticated and complex than earlier ones, capable of performing significantly more complex tasks. The therapeutic benefits of such devices have been well proven.

There are many implementations of implantable medical devices that provide data acquisition of important physiological data from a human body. Many implantable medical devices are used for cardiac monitoring and therapy. Often these devices include sensors that are placed in blood vessels and/or chambers of the heart and are operatively coupled with implantable monitors and therapy delivery devices. For example, such cardiac systems include implantable heart monitors and therapy delivery devices, such as pacemakers, cardioverter, defibrillators, heart pumps, cardiomyostimulators, ischemia treatment devices, drug delivery devices, and other heart therapy devices. Most of these cardiac systems include electrodes for sensing and gain amplifiers for recording and/or driving sense event signals from the inter-cardiac or remote electrogram (EGM).

As the functional sophistication and complexity of implantable medical device systems have increased over the years, it has become increasingly useful to include a system for facilitating communication between one implantable medical device and another implantable medical device or external device, for example, a programming console, monitoring system, or the like. Shortly after the introduction of the earliest pacemakers, it became apparent that it would be desirable for physicians to non-invasively obtain information regarding the operational status of the implantable medical device, and/or to exercise at least some control over the device, e.g., to turn the device on or off or adjust the pacing rate, after implant. As new, more advanced features have been incorporated into implantable medical devices, it has been increasingly useful to convey correspondingly more information to/from the device relating to the selection and control of those features.

Generally, a number of physiological data such as ventricular pressure, oxygen supply in the patient's blood, EGM data, a patient's breathing patterns, and the like, are collected and used by the devices implanted within a human body. The data can then be used to analyze the condition of a patient's physical state. Many times, information gathered by the implantable medical device may provide indications of certain conditions in a patient's body. The information gathered by the implantable medical devices may be used to validate and/or test new algorithms and/or firmware implemented into the implantable medical devices. However, information gathered by the implantable medical devices used to validate new algorithms and/or operations of the implantable medical devices may be limited and/or insufficient.

Exercise stress testing can be used to evaluate the proper functioning of the implantable medical device and/or the patient's health. In an exercise stress test, a patient walks on a treadmill, or pedals an exercise bicycle, at increasingly higher levels of physical exertion. The patient's heart rate and blood pressure increase with the levels of physical exertion. In a pharmacological stress test, a drug (e.g., dipyridamole, dobutamine, adenosine, etc.) is administered intravenously to increase heart rate and blood pressure in a manner similar to the effects of physical exertion. During exercise and pharmacological stress tests, the patient's heart rate and blood pressure are monitored. If the patient's heart tissue does not receive needed amounts of oxygen and nutrients, the patient experiences myocardial ischemia.

Non-invasive and free of chemical side effects, exercise stress tests are typically preferred over pharmacological stress tests. Invasive pharmacological stress tests are usually performed on patients that cannot tolerate exercise stress tests (e.g., patients with physical limitations such as back trouble, joint disease, marked fatigue, etc.).

Testing the responsiveness of the implantable medical device during particular activities such as stress testing, using current methodologies can be difficult. Often changes made to the operation of the implantable medical device, such as changes in the responsiveness of the device to certain physical activities, may be difficult to confirm and qualify. In some cases, an inordinate number of testing processes must be performed to validate and/or check the effectiveness of the responsiveness of the implantable medical device, particularly when modifications to the responsiveness have been implemented.

SUMMARY OF THE INVENTION

In one aspect of the present invention, a method is provided for implementing external data within an implantable medical device. A first stress test is performed using an external sensor. External data resulting from the initial stress test is acquired. An external data injection process is performed. The external data injection process includes providing the external data to the implantable medical device. A second stress test is performed, the second stress test being substantially similar to the first stress test. Internal data resulting from the second stress test is acquired. Internal data resulting from the second stress test along with the external data resulting from the first stress test, are processed.

In another aspect of the present invention, an apparatus is provided for implementing external data within an implantable medical device. The apparatus includes a processor and a control logic unit operatively coupled to the processor, the control logic unit generating at least one control signal in response to a command from the processor. A data acquisition controller is operatively coupled with the control logic unit, the data acquisition controller acquiring internal data in response to an assertion of at least one control signal from the control logic unit. A memory unit is operatively coupled with the data acquisition controller, the memory unit storing the acquired physiological data and injected external data. A telemetry unit is operatively coupled with the processor and the memory unit, the telemetry unit receiving external data relating to a first stress test, and a firmware unit is operatively coupled with at least one of the processor, the control unit, and the memory unit, the firmware unit processing internal data resulting from a second stress test with the external data.

In yet another aspect of the present invention, a system is provided for implementing external data into an implantable medical device and includes an external sensor device to acquire external data resulting from a first stress test and an implantable medical device adapted to acquire data related to a patient's body and provide a therapy in response to the data. The implantable medical device stores the external data, acquires internal data relating to a second stress test, and processes the external and internal data to validate the operation of the implantable medical device. An access device transfers data from the external sensor device to the implantable medical device, and at least one sensor is operatively coupled to the implantable medical device, the sensor providing the internal data to the implantable medical device.

BRIEF DESCRIPTION OF THE DRAWINGS

The inventions may be understood by reference to the following description taken in conjunction with the accompanying drawings, in which like reference numerals identify like elements, and in which.

Figure 1:
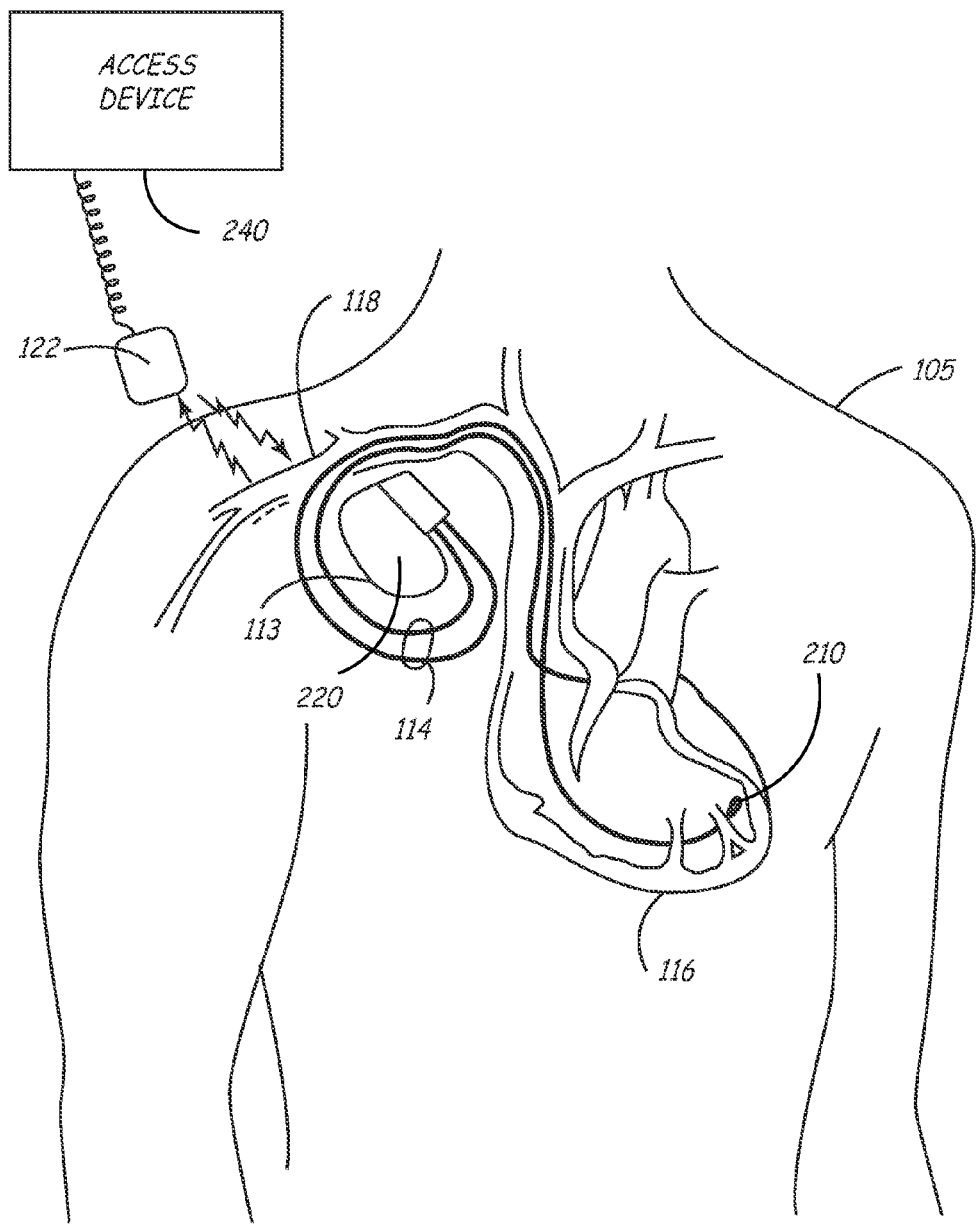
FIG. 1 is a simplified diagram of an implementation of an implantable medical device, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involving the operation of implantable medical devices (e.g., pacemakers, cardio defibrillators, the like). The operation of an implantable medical device include collecting, storing, and analyzing physiological data relating to a patient, and/or delivering therapy (e.g., cardiac therapy) to a portion of a patient's body. Often, these tasks are performed by an implantable medical system, which includes an implantable medical device. Based upon the analysis performed by the implantable medical system, one or more therapies may be delivered to a particular portion of a patient's body. One example of such a therapy is a cardiac therapy, which is delivered to a patient's heart. Interpretation of the physiological data and/or data relating to unusual activities in the patient's body is important in determining the behavior (e.g., therapy deliver patterns, etc.) of the implantable medical device.

Embodiments of the present invention provide for injecting external data, such as data acquired from an external accelerometer, into an implantable medical device. Embodiments of the present invention provide for using the external data in combination with internal data (i.e., data acquired by sensors operatively coupled with the implantable medical device) to validate the operation of the implantable medical device. Embodiments of the present invention provide for injecting external data (e.g., test data) acquired during a controlled activity test (e.g., treadmill exercise test) into an implantable medical device and repeating the controlled activity test using the injected external data to validate the operation of the implantable medical device.

Turning now to FIG. 1, one embodiment of implementing an implantable medical device into a human body is illustrated. A sensor/therapy delivery device 210 (e.g., devices attached to leads 114) placed within the heart of the human body 105 is used to acquire and process physiological data. An implantable medical device 220 collects and processes a plurality of data acquired from the human body 105. In one embodiment, the implantable medical device 220 may be a pacemaker or a defibrillator. The data acquired by the implantable medical device 220 can be monitored by an external system, such as the access device 240, comprising a programming head 122, which remotely communicates with the implantable medical device 220. The programming head 122 is utilized in accordance with medical device programming systems known to those skilled in the art having the benefit of the present disclosure, for facilitating two-way communication between the implantable medical device 220 (e.g., pacemaker) and the access device 240.

In one embodiment, a plurality of access devices 240 can be employed to collect a plurality of data processed by the implantable medical device 220 in accordance with embodiments of the present invention. The implantable medical device 220 is housed within a hermetically sealed, biologically inert outer canister or housing 113, which may itself be conductive so as to serve as an electrode in the implantable medical device 220 pacing/sensing circuit. One or more pacemaker sensors/leads, collectively identified with reference numeral 114 in FIG. 1, are electrically coupled to the implantable medical device 220 and extend into the patient's heart 116 via a vein 118. Disposed generally near a distal end of the leads 114 are one or more exposed conductive electrodes (sensor/therapy delivery device 210) for receiving electrical cardiac signals or delivering electrical pacing stimuli to the heart 116. The leads 114 may be implanted with their distal end situated in either the atrium or ventricle of the heart 116. In an alternative embodiment, the sensor/therapy delivery device 210, or the leads 114 associated with the sensor/therapy delivery device 210, may be situated in a blood vessel on the heart 116, such as a vein 118.

In one embodiment, the implantable medical device 220 illustrated in FIG. 1 is capable of performing a rate-responsive treatment based on physiological and/or non-physiological data detected by the implantable medical device 220. One method of performing a rate responsive therapy delivery is to determine a target rate based upon predetermined programming for the operation of the implantable medical device 220 and new physiological data and other data sensed from the patient's body 105. The data sensed from the patient's body 105 may include data from sensors that detect a patient's activity, body movements (accelerations experienced by the patient), oxygen levels in the patient's blood, EGC readings, and the like. The rate responsive pacing rate (or target pacing rate TPR) may be defined by Equation 1 as:

$$TPR = \text{Predetermined Pacing Rate} + f(\text{Sensor Data}) \quad \text{Equation 1}$$

wherein f(Sensor Data) is typically a linear or monotonic function of the sensor data.

One method of performing a rate responsive therapy delivery is by calculating the patient's minute ventilation. Minute ventilation has be en demonstrated clinically to be a parameter that correlates directly to the actual metabolic and physiologic needs of the patient 105. Minute ventilation (MV) may be defined by Equation 2 as:

$$MV = \text{Respiration Rate} \times \text{Tidal Volume} \quad \text{Equation 2}$$

wherein the respiration rate is represented by breaths per minute taken by the patient 105 and the tidal volume is represented in volume in liters (e.g., volume of air intake into the lungs on the patient 105). In one embodiment, the implantable medical device 220 measures changes in the transthoracic impedance, which is generally proportional to minute ventilation. Since minute ventilation is a function of the respiration rate and the tidal volume (see Equation 2), the minute ventilation may be a physiological indicator of changes in the metabolic demands in a patient's body 105, which may provide an indication of an adjustment to therapy delivery rate provided by the implantable medical device 220. One exemplary method of performing a rate responsive therapy delivery may be found in U.S. Pat. No. 5,562,711, "Method and Apparatus For Rate-Responsive Cardiac Pacing."

Figure 2:
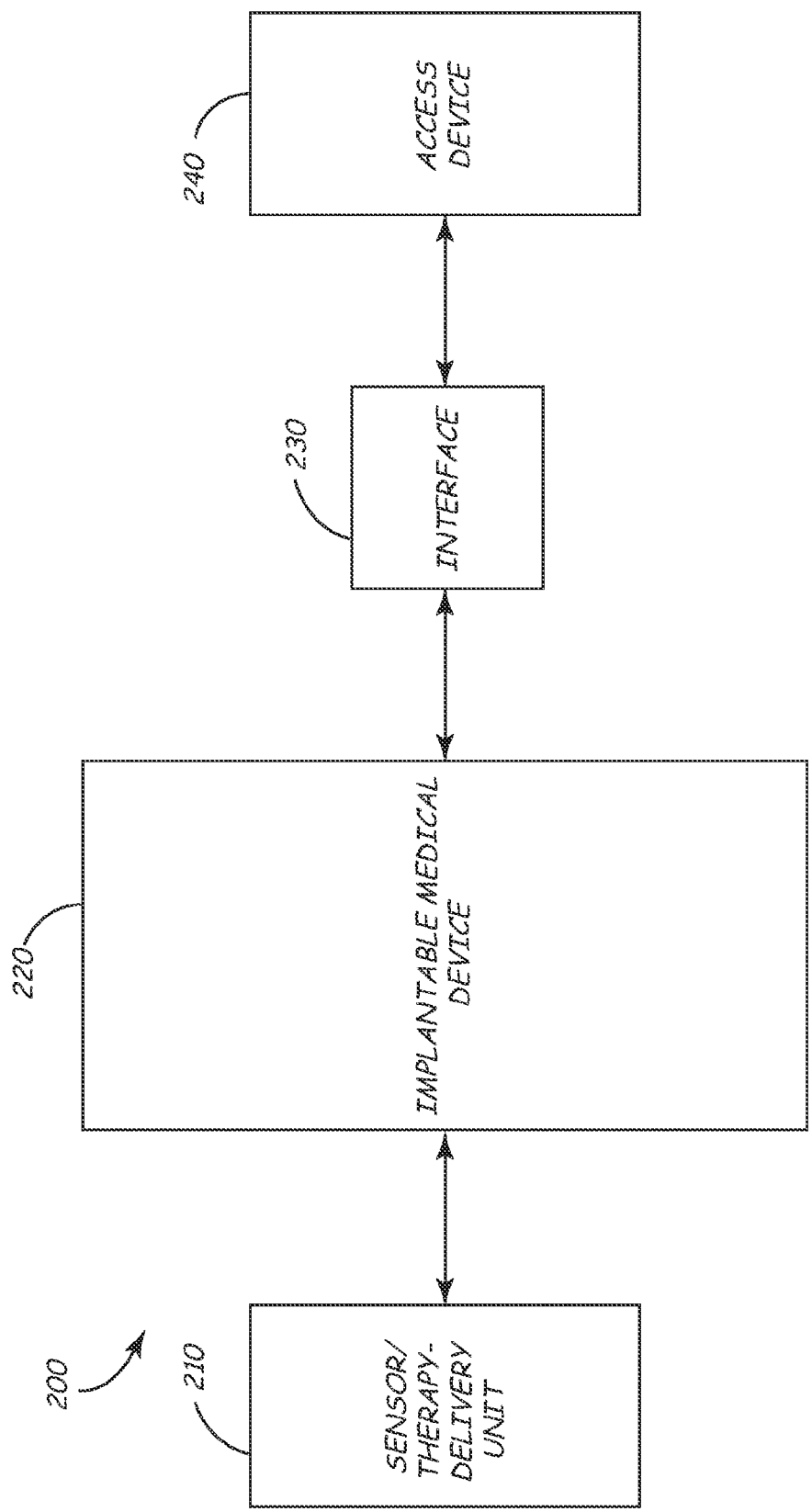
FIG. 2 is a simplified block diagram representation of an implantable medical system in accordance with one illustrative embodiment of the present invention.

Turning now to FIG. 2, a system 200, in accordance with an embodiment of the present invention, is illustrated. The system 200 includes a sensor/therapy delivery unit 210, an implantable medical device 220, and an access device 240. Embodiments of the present invention provide a plurality of physiological data and non-physiological data from the sensor/therapy delivery unit 210 to the implantable medical device 220, which are then processed and stored in the implantable medical device 220. The sensor/therapy delivery unit 210 may include a plurality of sensors that are capable of acquiring physiological and non-physiological data. Based upon data from the sensor(s) 210 and other factors, the implantable medical device 220 may deliver a therapy to a portion of the patient's body 105, via the sensor/therapy delivery unit 210. The access device 240 can be used to reprogram and/or make modifications to the operation of the implantable medical device 220.

Figure 3:
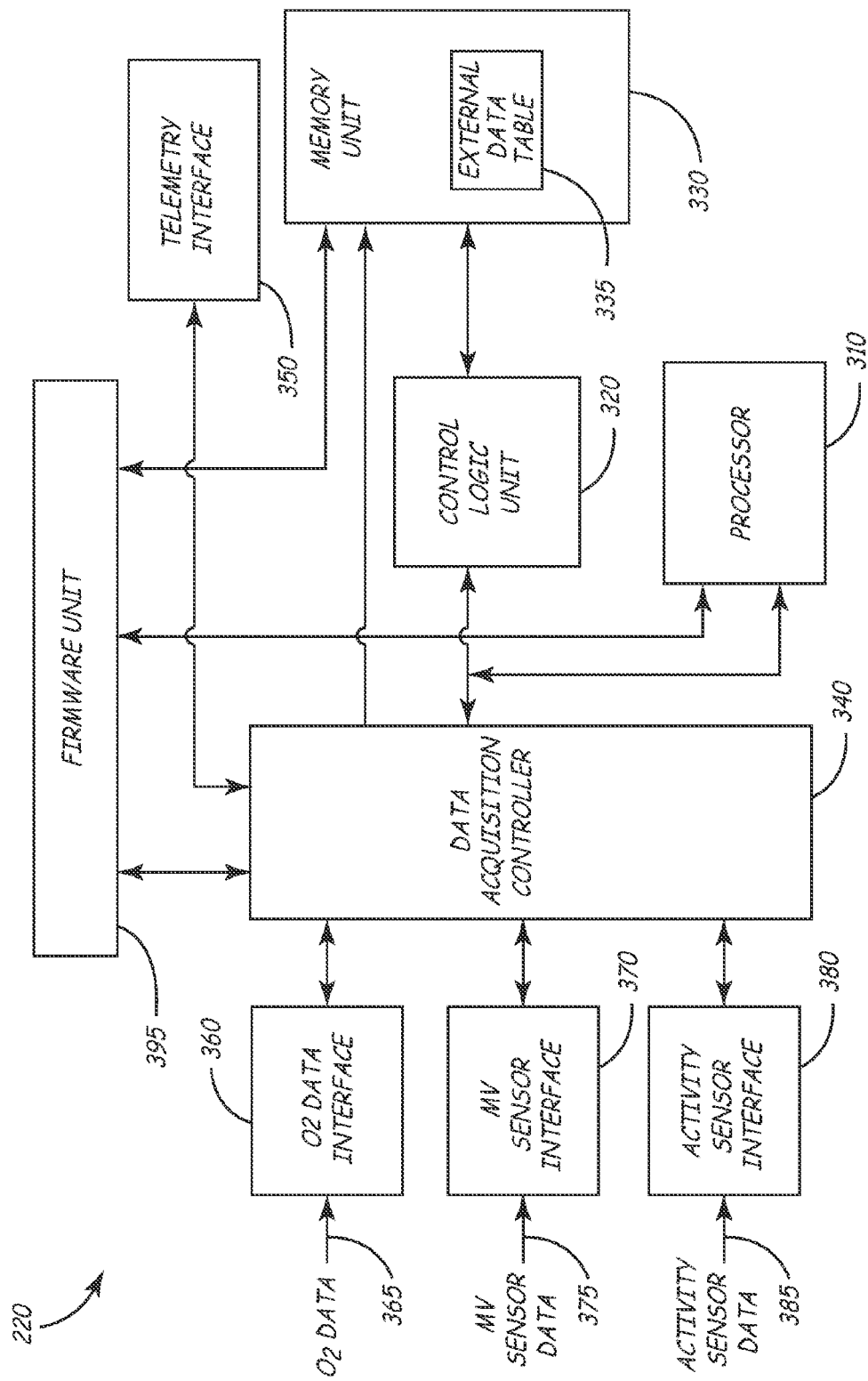
FIG. 3 is a more detailed block diagram representation of the implantable medical device of FIGS. 1 and 2, in accordance with one embodiment of the present invention.

Turning now to FIG. 3, a more detailed block diagram depiction of one embodiment of the implantable medical device 220 is illustrated. The implantable medical device 220 includes a processor 310, a control logic unit 320, a memory unit 330, a data acquisition controller 340, a telemetry interface 350, an $O_2$ data interface 360, an MV sensor interface 370, and an activity sensor interface 380. In one embodiment, other sensor interfaces may be operatively coupled to the data acquisition controller 340. Processor 310 controls the operation of the implantable medical device 220, and utilizes the control logic unit 320 to perform a plurality of operations, including memory access and storage operations. Processor 310 communicates with the control logic unit 320 and the data acquisition controller 340 via a bus line.

Control logic unit 320 sends control signals to the memory unit 330 for controlling and installing memory unit 330, and to the data acquisition controller 340, which controls the acquisition of physiological data and drives output signals to the telemetry interface 350.

In one embodiment, the telemetry interface 350 is capable of facilitating real-time access of physiological data acquired by the data acquisition controller 340. Therefore, a physician can view physiological data on a real-time basis by accessing the data acquisition controller 340, via the telemetry interface 350. The telemetry interface 350 can be used to download modifications to the firmware that is used to operate the implantable medical device 220. The data acquisition controller 340 can prompt the data interfaces 360, 370, 380 to retrieve physiological data, process such data, and deliver physiological data to the data acquisition controller 340. The data interfaces 360, 370, 380 can perform a number of analog-to-digital conversions and time-interval conversions, known to those skilled in the art, upon the acquired physiological data. The data interfaces 360, 370, 380 can acquire, condition, and process physiological data and forward them to the data acquisition controller 340.

The minute ventilation sensor interface 370 is capable of receiving data from a minute ventilation sensor. The minute ventilation sensor interface 370, in one embodiment, may condition the accelerometer data received from an accelerometer and forward the conditioned data to the data acquisition controller 340. Furthermore, the activity sensor interface 380 receives data from an activity sensor, which in one embodiment may be a piezoelectric device, and conditions such data and forwards the conditioned data to the data acquisition controller 340.

As illustrated in FIG. 3, implantable medical device 220 further includes a firmware unit 395. The firmware unit 395, in one embodiment, includes a plurality of sets of program/descriptive-language circuitry/logic circuitry that may be programmed. Sections of the firmware unit 395 can provide controllability of the operations of the implantable medical device 220. In one embodiment, the firmware unit 395, in conjunction with the processor 310, controls the operation of the implantable medical device 220.

The memory unit 330 includes an external data table 335 capable of storing sensor data acquired from an external source (external sensor data). External sensor data can be downloaded into the memory unit 330 and into the external data table 335, via the access device 240. In an alternative embodiment, external sensor data, or external data, can be downloaded into the external data table 335 via the telemetry interface 350. In one embodiment, real-time external data sensor capture may be placed into the memory unit 330 via the telemetry interface 350.

Figure 4:
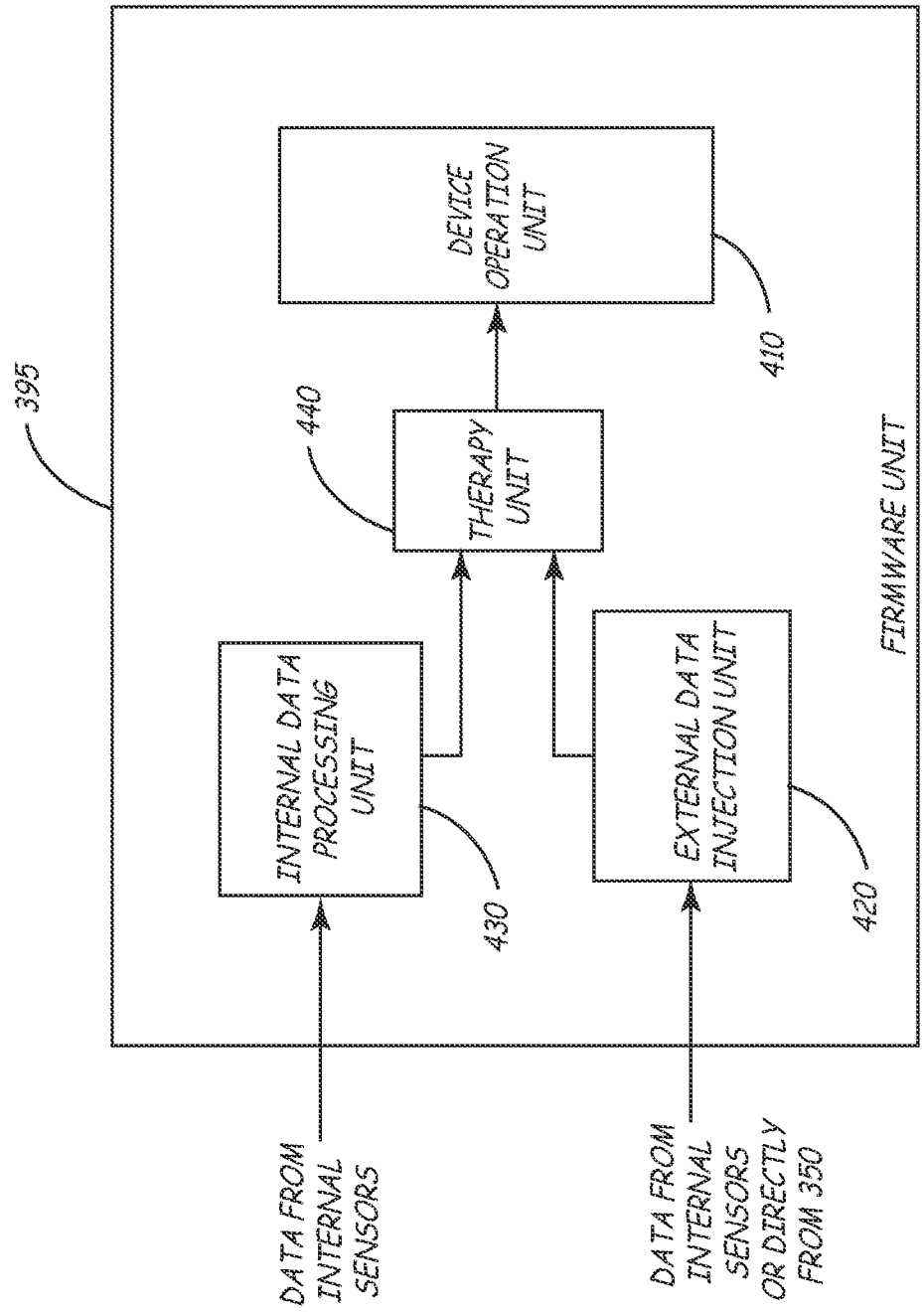
FIG. 4 is a more detailed block diagram representation of the firmware unit of FIG. 3, in accordance with one embodiment of the present invention.

Turning now to FIG. 4, a simplified block-diagram representation of one embodiment of the firmware unit 395, is illustrated. In one embodiment, the firmware unit 395 includes a device operation unit 410, an external data injection unit 420, an internal data processing unit 430, and a therapy unit 440. Data from internal sensors (i.e., sensors placed inside the patient's body and operatively coupled with the implantable medical device) such as an MV (minute voltage) sensor, an R2 data sensor, and/or an activity sensor (a pezio-electronic ceramic device) is acquired by the internal data processing unit 430 for processing. Further, data from an external sensor (e.g., an accelerometer attached onto a patient's body) is acquired by the external data injection unit 420.

In one embodiment, the external data injection unit 420 receives stored external sensor data from the external data table 335 in the memory unit 330. Utilizing the external data injection unit 420, external data can be injected into the implantable medical device 220, along with the internal sensor data, which are both sent to the therapy unit 440. The therapy unit 440 processes the external sensor data and the internal sensor data to determine a therapy delivery schedule. In one embodiment, the therapy unit 440 is capable of performing a rate responsive therapy delivery based upon the internal sensor data and the external sensor data.

The device operation unit 410 includes software, firmware, and/or hardware that provide logic for performing a plurality of operations as employed by the implantable medical device 220. For example, the therapy delivery schedule determined by the therapy unit 440 is used by the device operation unit 410 to prompt the implantable medical device 220 to deliver therapies based upon the data from therapy unit 440.

Figure 5:
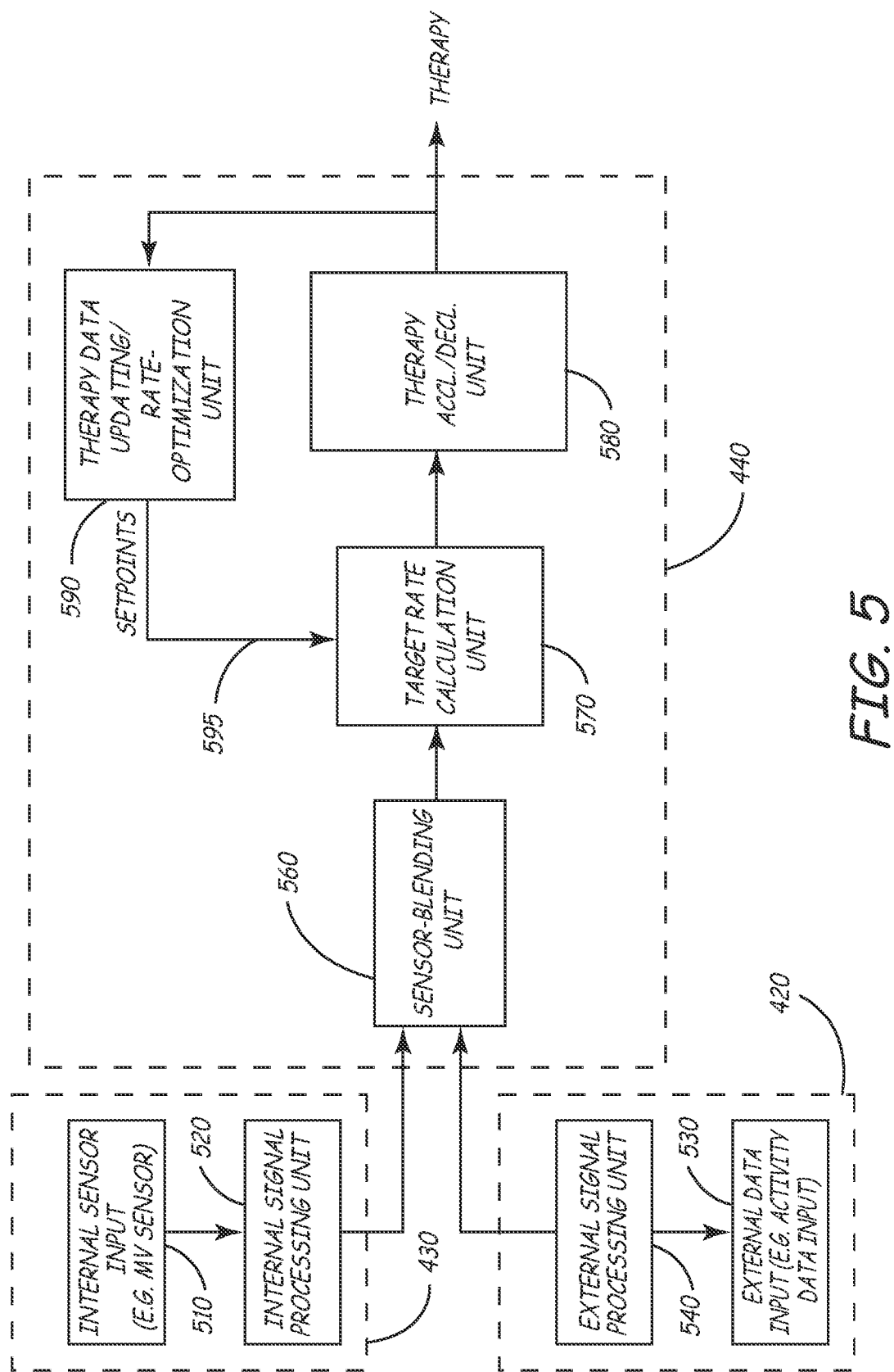
FIG. 5 is a more detailed block diagram representation of the therapy unit of FIG. 4, and its surrounding structures, in accordance with one embodiment of the present invention.

Turning now to FIG. 5, a more detailed block-diagram depiction of the interaction between the external data injection unit 420, the internal data processing unit 430, and the therapy unit 440, is illustrated. In one embodiment, the internal data processing unit 430 includes an internal sensor input 510 and an internal signal processing unit 520. The internal signal processing unit 520 processes the internal sensor input 510. The internal sensor input 510 may be internal sensor data, such as an MV sensor input. Similarly, the external signal processing unit 540 may send external sensor data to the therapy unit 440. The external data injection unit 420 includes an external signal processing unit 540, which processes the external data input 530. The external data may include sensor data from an external device such as an accelerometer.

In one embodiment, the therapy unit 440 includes the sensor-blending unit 560, a target rate calculation unit 570, a therapy accelerator/decelerator unit 580, and a therapy data updating/rate optimization unit 590. The sensor-blending unit 560 acquires the processed internal sensor data from the internal signal processing unit 520 and the processed external sensor data from the external signal processing unit 540 and combines the data. In one embodiment, the sensor-blending unit 560 blends the MV sensor data with corresponding accelerometer data (external sensor data).

The data from the sensor-blending unit 560 is sent to the target rate calculation unit 570 for determining a target pacing rate of the therapy to be delivered based upon the input received (blending of the MV data and the accelerometer data). Therefore, physiological and non-physiological changes experienced by the patient will drive a change in the therapy rate to accommodate for particular activities, such as exercise, for example. The target rate calculation unit 570 uses a setpoint rate of therapy delivery, and modifies the setpoint rate based upon data from the sensor-blending unit 560. Based upon the target pacing rate calculations, the therapy accelerator/decelerator unit 580 reduces or increases the therapy rate.

The therapy delivered by the implantable medical device 220 may be based upon the reduced or increased therapy rate, as determined by the therapy accelerator/decelerator unit 580. Furthermore, this therapy rate is fed back to the therapy data updating/rate optimization unit 590. The unit 590 updates histogram bins that store the histograms relating to the operation of the implantable medical device 220. Furthermore, a rate profile optimization is performed by the therapy data updating/rate optimization unit 590 to optimize the therapy rate based upon longer-term data from the patient's body 105 (e.g., performed once a day). The therapy data updating/rate optimization unit 590 provides a setpoint therapy target pacing rate to the target rate calculation unit 570 via a line 595, completing the feedback loop illustrated in FIG. 5. Therefore, therapy delivered to the patient is monitored and adjusted depending on the activities and/or the physiological needs of the patient.

Figure 6:
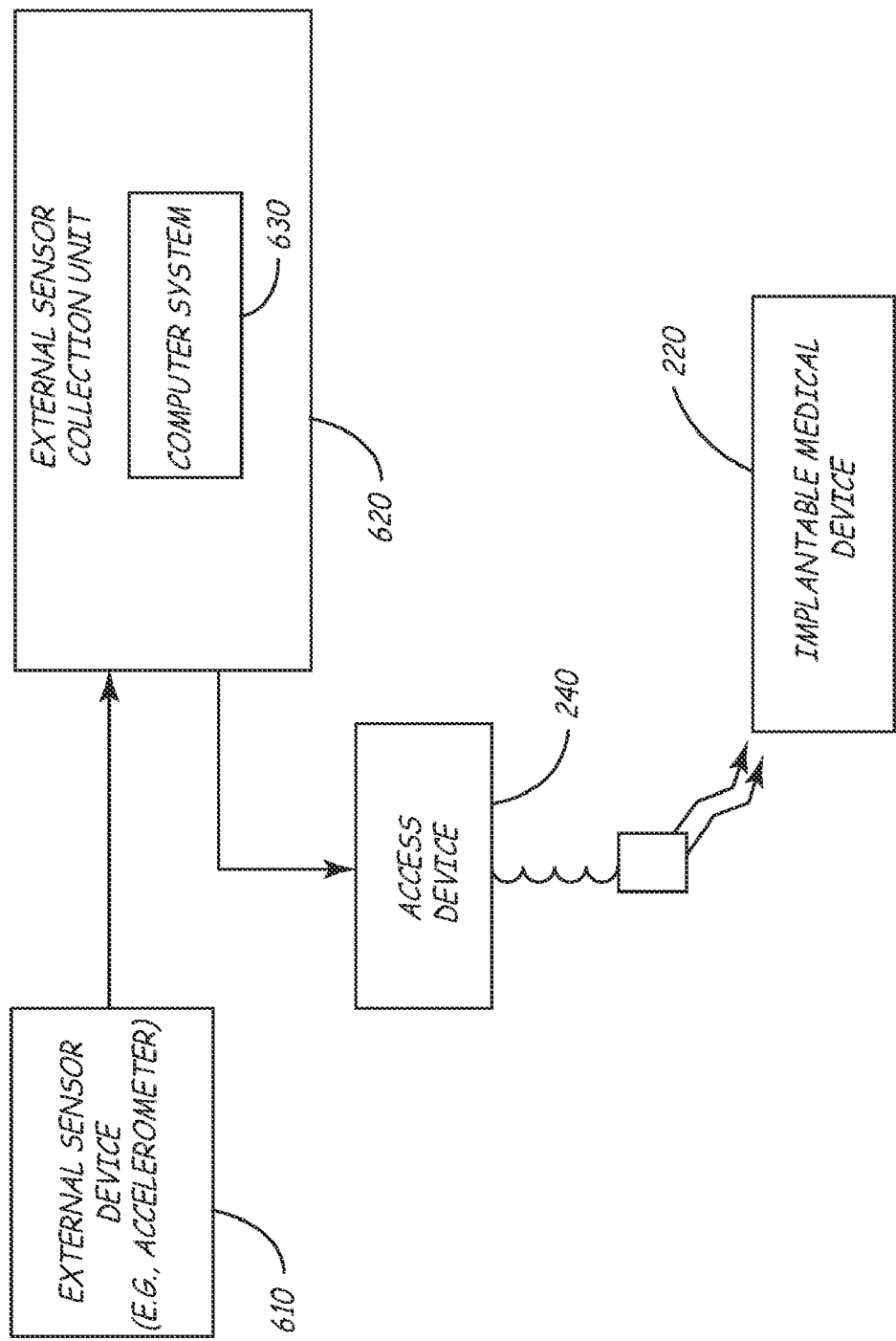
FIG. 6 is a block diagram representation of a system, interconnecting an external sensor to the implantable medical device, in accordance with one embodiment of the present invention.

Turning now to FIG. 6, a block diagram representation of the process of injecting external data into the implantable medical device 220, is illustrated. As illustrated in FIG. 6, according to the present invention, an external sensor device 610 (e.g., an accelerometer) acquires external data from the patient's body 105. The data from the external sensor device 610 is provided to an external sensor collection unit 620 that acquires and stores the external sensor data. In one embodiment, the external sensor collection unit 620 includes a computer system 630 that includes memory for storing such data. Data from the external sensor collection unit 620 is then provided to the access device 240.

In one embodiment, the access device 240 downloads the external data into the implantable medical device 220. In one embodiment, the downloading of the external data is performed via wireless connections. The access device 240 downloads the external sensor data into the external data table 335 in the memory unit 330 of the implantable medical device 220. In an alternative embodiment, the external data may be collected in a real-time manner and provided to the access device 240 for real-time downloading into the implantable medical device 220, via the telemetry interface 350. Therefore, external data from an initial stress test can be downloaded into the implantable medical device 220. A subsequent test (e.g., stress test) may then be performed by the patient, wherein the implantable medical device 220 analyzes results from the subsequent stress test, using the stored external stress data. In one embodiment, the subsequent stress test (i.e., second stress test) is substantially similar to the initial stress test (i.e., first stress test). In one embodiment, the stored external stress data may be approximately equivalent to external data that would be generated during the subsequent stress test.

Figure 7:
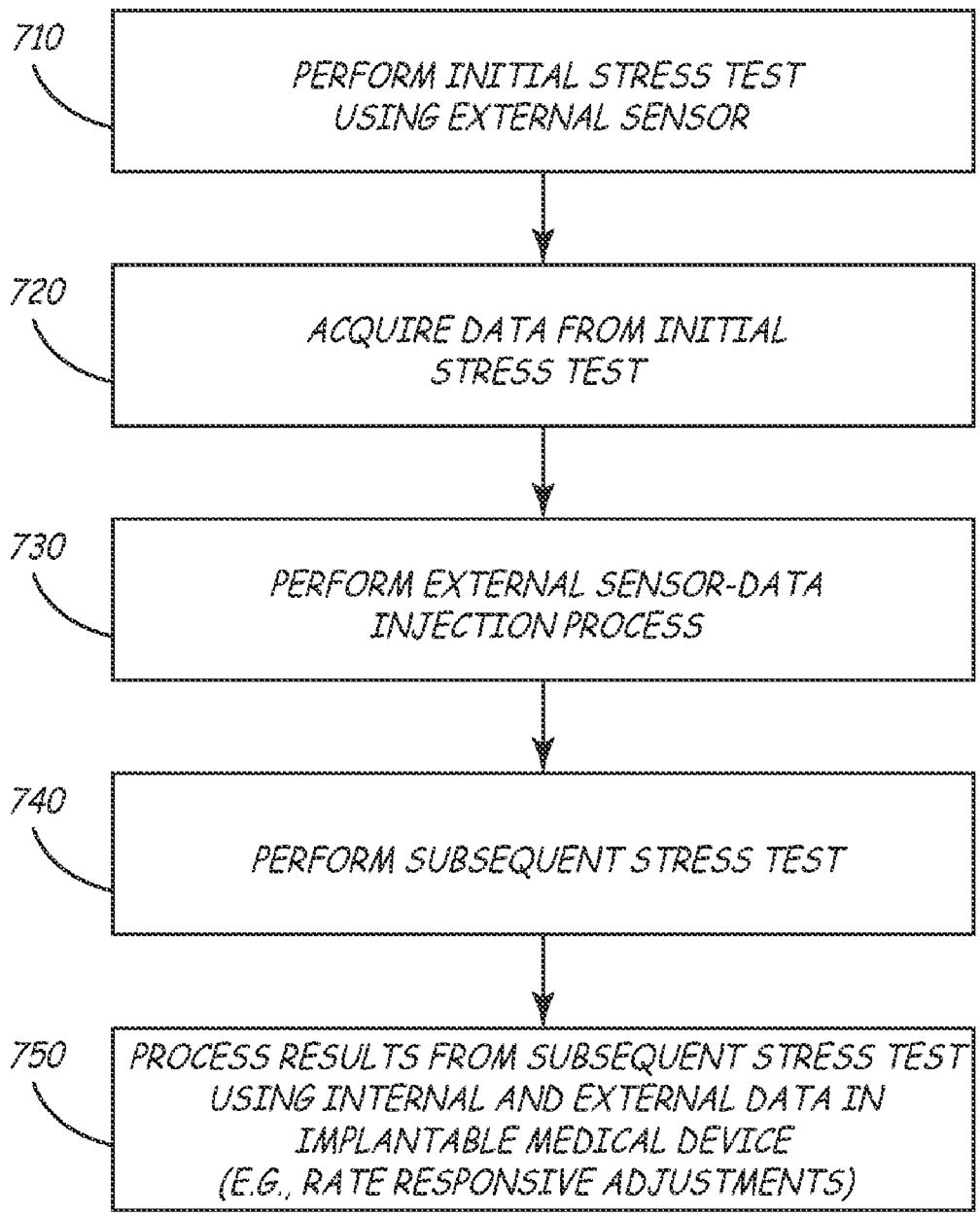
FIG. 7 is a flowchart depiction of a method, in accordance with one illustrative embodiment of the present invention.

Turning now to FIG. 7, a method in accordance with an embodiment of the present invention, is illustrated. An initial stress test using an external sensor is performed by a patient (block 710). In one embodiment, the initial stress test is performed by the patient, upon whom a strap-on external sensor, such as a strap-on accelerometer, may be attached. Data from the external sensor is acquired from the initial stress test (block 720). In other words, the strap-on accelerometer acquires data from the patient's body 105 during the initial stress test.

Figure 8:
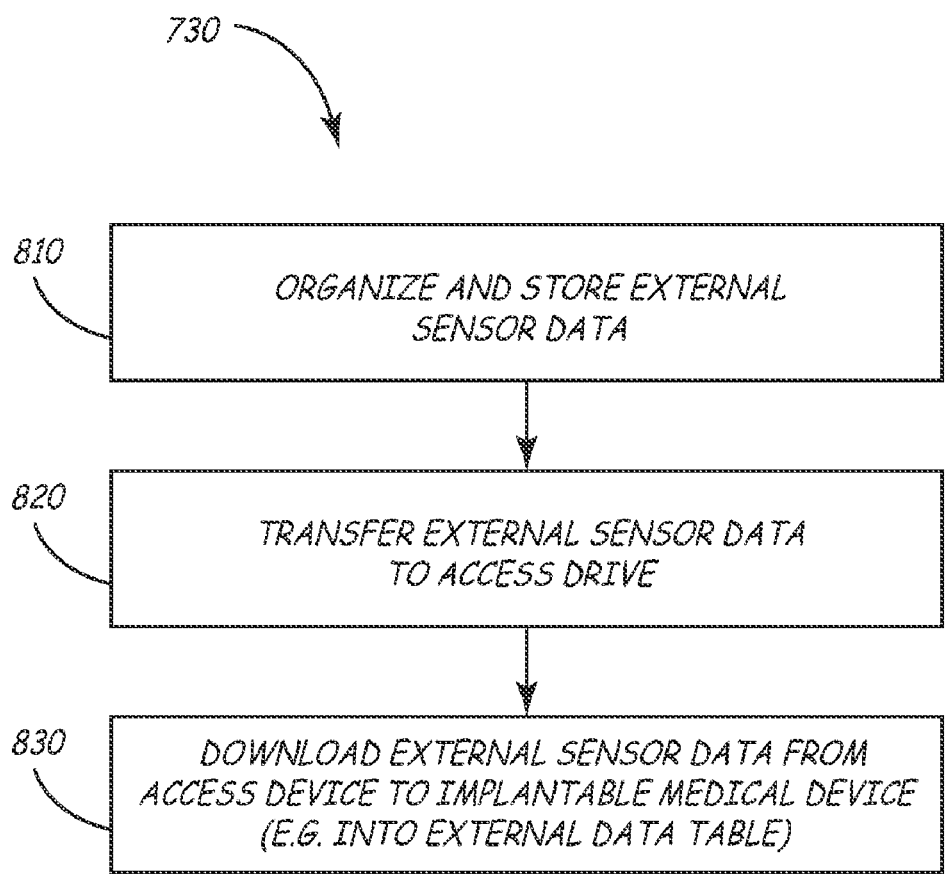
FIG. 8 is a more detailed flowchart depiction of performing an external sensor data injection process, as indicated in FIG. 6, in accordance with one illustrative embodiment of the present invention.

An external sensor data injection process is then performed in order to transmit the external acquired sensor data into the implantable medical device 220 (block 730). A more detailed illustration of performing the external sensor data injection process indicated in block 730 is shown in FIG. 8 and the accompanying description below. When the external sensor data injection process is substantially complete, a subsequent stress test is performed by the patient (block 740). In this case, the downloaded external stress test data from the initial stress test is analyzed by the implantable medical device 220, along with the real-time internal sensor data, during the performance of the subsequent stress test.

The system 200 then processes the results from the subsequent stress test using the internal and external data in the implantable medical device 220 (block 750). For example, the implantable medical device 220 may perform rate-responsive adjustments based upon the real-time internal sensor data and the stored external sensor data on the previous stress test during the subsequent stress test. Furthermore, a new algorithm applied within the implantable medical device 220 may be tested and/or validated using the processing of the results from the subsequent stress test. A more detailed description of the steps for performing the step indicated in block 750 is illustrated in FIG. 9 and the accompanying description below.

Turning now to FIG. 8, a more detailed flowchart depiction of the process of performing the external sensor data injection process indicated in block 730 of FIG. 7 is illustrated. The system 200 organizes and stores the acquired external sensor data (block 810). In one embodiment, the external sensor data is organized and stored within the external sensor collection unit 620, which includes the computer system 630 with corresponding memory within the computer system 630. Once the system 200 organizes and stores the external sensor data, the data is then transferred to the access device 240 (block 820). In one embodiment, the access device 240 includes memory for storing the transferred external sensor data.

Subsequently, the access device 240 downloads the external sensor data from the access device 240 to the implantable medical device 220 (block 830). In one embodiment, the access device 240 downloads the external sensor data into the external data table 335 in the memory unit 330. In an alternative embodiment, the external sensor data may be downloaded from the access device 240 into the implantable medical device 220 in a real-time, or near real-time, fashion via the telemetry interface 350. The completion of the steps described in FIG. 8 substantially completes the external sensor unit injection process described in block 730 of FIG. 7.

Figure 9:
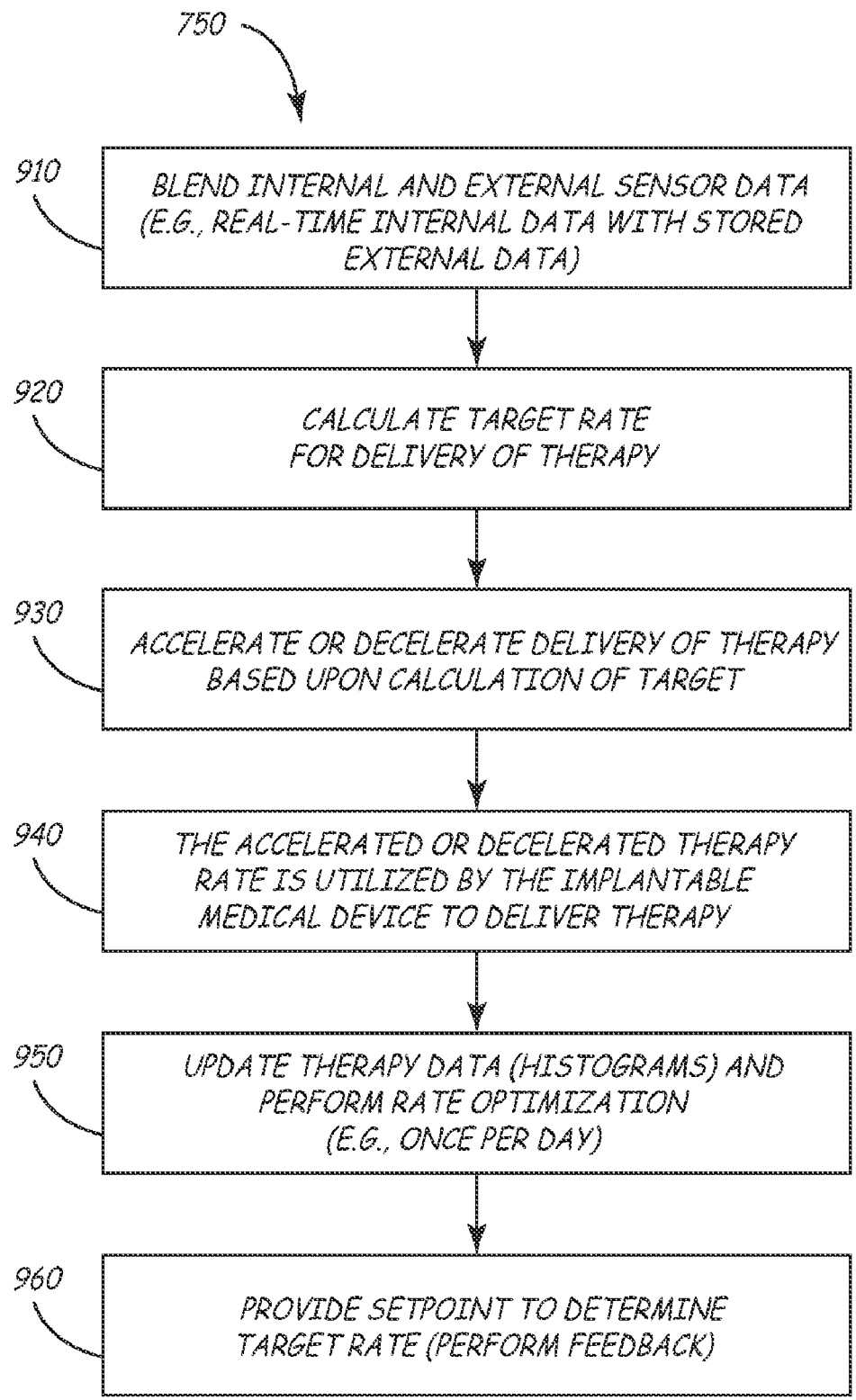
FIG. 9 is a more detailed flowchart depiction processing results from a subsequent stress test using internal and external data, as indicated in FIG. 6, in accordance with one illustrative embodiment of the present invention.

Turning now to FIG. 9, a more detailed flowchart depiction of the step of processing results from the subsequent stress test, using internal and external data in the implantable medical device 220, as indicated in block 750 of FIG. 7, is illustrated. The implantable medical device 220 blends internal and external sensor data (block 910). The internal sensor data that is acquired during the subsequent stress test is combined/blended with the external sensor data from the previous stress test, which corresponds to the internal sensor data during the subsequent stress test. In other words, real-time internal sensor data is combined with stored external data. The implantable medical device 220 then calculates a target pacing rate for delivery of therapy to a portion of the patient's body 105 (e.g., cardiac therapy), as indicated in block 920 of FIG. 9. The calculation of the target pacing rate, in one embodiment, is performed by the target rate calculation unit 570, based upon an initial setpoint rate for delivering therapy.

Once the target rate for delivery of therapy is calculated, the implantable medical device 220 accelerates or decelerates the delivery of therapy based upon the calculation (block 930). In one embodiment, data from the target rate calculation unit 570 is provided to the therapy accelerator/decelerator unit 580, which adjusts the therapy delivery rate. In one embodiment, the accelerated or decelerated therapy rate is utilized by the implantable medical device 220 to deliver the therapy (block 940).

The implantable medical device 220 also performs an updating of the therapy data and rate optimization of the therapy rate (block 950). Histograms relating to the therapy and physiological data of the patient 105 are updated using the new therapy rate. Furthermore, the therapy rate is optimized based upon longer-term data relating to the patient 105. In one embodiment, the rate optimization is performed at a rate of once per day. Updating of the therapy data and performing the rate optimization will provide for a new setpoint rate of therapy, which may be used to determine a new target rate (block 960).

The setpoint is provided to the target rate calculation unit 570 as feedback data, which is used as a baseline value to calculate a new target rate in response to new sensor data received. In one embodiment, the steps described in FIG. 9 are performed by the therapy unit 440, which in one embodiment is a part of the firmware unit 395. Substantial completion of the steps described in FIG. 9 completes the processing of results from subsequent stress tests using internal sensor data and external sensor data from an initial stress test, as indicated in block 750 of FIG. 7. Using the processes described above, testing, developing, and validating algorithms programmed into the implantable medical device 220 may be performed.

The above detailed description is an illustrative example of an embodiment in accordance with the present invention, of the implementation of the implantable medical device 220 described above. It should be appreciated that other implementations and/or embodiments can be employed within the spirit of the present invention. The teachings of the present invention can be utilized for a variety of systems relating to electrical circuitry, including circuitry that utilize stored charge.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is set forth in the claims below.

What is claimed:

1. A method for injecting external data into an implantable medical device, comprising the steps of:

performing a first stress test using an external sensor;

acquiring external data resulting from said first stress test;

performing an external data injection process, said external data injection process comprising providing said external data to said implantable medical device;

performing a second stress test, said second stress test being substantially similar to said first stress test;

acquiring internal data resulting from said second stress test; and processing said internal data resulting from said second stress test along with said external data resulting from said first stress test.

2. The method described in claim 1, wherein the step of performing a first stress test using an external sensor further comprises performing said first stress test on a treadmill.

3. The method described in claim 1, wherein the step of acquiring external data resulting from said initial stress test further comprises acquiring non-physiological data.

4. The method described in claim 3, wherein the step of acquiring external data resulting from said initial stress test further comprises acquiring data from an external accelerometer.

5. The method described in claim 1, wherein the step of performing an external data injection process further comprises:

storing said external data;

transferring said stored external data to an access device capable of communicating with said implantable medical device; and downloading said external data from said access device into said implantable medical device.

6. The method described in claim 1, wherein the step of acquiring internal data resulting from said second stress test further comprises acquiring data from an internal sensor operatively coupled with said implantable medical device.

7. The method described in claim 6, wherein the step of acquiring internal data resulting from said second stress test further comprises acquiring physiological data.

8. The method described in claim 1, wherein the step of processing said internal data resulting from said second stress test along with said external data resulting from said first stress test further comprises:

blending said internal data with said external data;

calculating a target pacing rate for a delivery of therapy based at least partially upon at least one of said blending of said internal and external data and an initial setpoint therapy target pacing rate;

modifying a therapy delivery rate based upon said target pacing rate; and calculating a new setpoint therapy target pacing rate as feedback for calculating a subsequent target pacing rate.

9. The method described in claim 8, wherein the step of blending said internal data with said external data further comprises combining real time physiological data with corresponding stored non-physiological data.

10. The method described in claim 1, wherein the step of processing said internal data resulting from said second stress test along with said external data resulting from said first stress test further comprises validating an operation of an implantable medical device.

* * * * *